United States Patent
Gramnäs

[11] Patent Number: 5,376,133
[45] Date of Patent: Dec. 27, 1994

[54] AN ADJUSTABLE RESILIENT FOOT PROSTHESIS

[76] Inventor: Finn Gramnäs, 511 56, Kinna, Sweden

[21] Appl. No.: 941,040
[22] PCT Filed: Mar. 28, 1991
[86] PCT No.: PCT/SE91/00239
  § 371 Date: Oct. 1, 1992
  § 102(e) Date: Oct. 1, 1992
[87] PCT Pub. No.: WO91/15171
  PCT Pub. Date: Oct. 17, 1991

[30] Foreign Application Priority Data
  Apr. 2, 1990 [SE] Sweden .......... SE9001184-2

[51] Int. Cl.⁵ .............................. A61F 2/62
[52] U.S. Cl. ........................ 623/38; 623/47; 623/53; 602/27
[58] Field of Search ......... 623/53, 38, 47, 52, 623/40–42, ; 602/27, 28

[56] References Cited

U.S. PATENT DOCUMENTS

| | | | |
|---|---|---|---|
| 35,686 | 6/1882 | Jewett | 623/38 X |
| 1,049,862 | 1/1913 | Hodge et al. | 623/52 |
| 3,461,464 | 8/1969 | Lindgren | 623/38 |
| 4,446,580 | 5/1984 | Furuya et al. | 623/53 |
| 4,865,611 | 9/1989 | Al-Turaiki | 623/47 X |

FOREIGN PATENT DOCUMENTS

| | | | |
|---|---|---|---|
| 2827092 | 1/1980 | Germany | 403/46 |
| 2163961 | 3/1986 | United Kingdom | 623/53 |
| 0262319 | 1/1970 | U.S.S.R. | 623/47 |

*Primary Examiner*—David H. Willse
*Attorney, Agent, or Firm*—Gardner, Carton & Douglas

[57] ABSTRACT

An artificial foot which includes a foot blade and a hollow cylindrical body which extends at an angle to the foot blade and which is connected thereto in a manner to permit relative movement therebetween. The foot also includes a two-part brace which is displaceable and adjustably mounted in an upper end of the cylindrical body and is attached to the foot blade at a lower end of the body in a manner such as to permit relative movement between the foot blade and the brace. Displaceability and adjustability of the brace, and therewith angular adjustment of the foot, may be provided by the combination of a ball screw and a ball nut which is rotatable, and selectively lockable by the user.

4 Claims, 3 Drawing Sheets

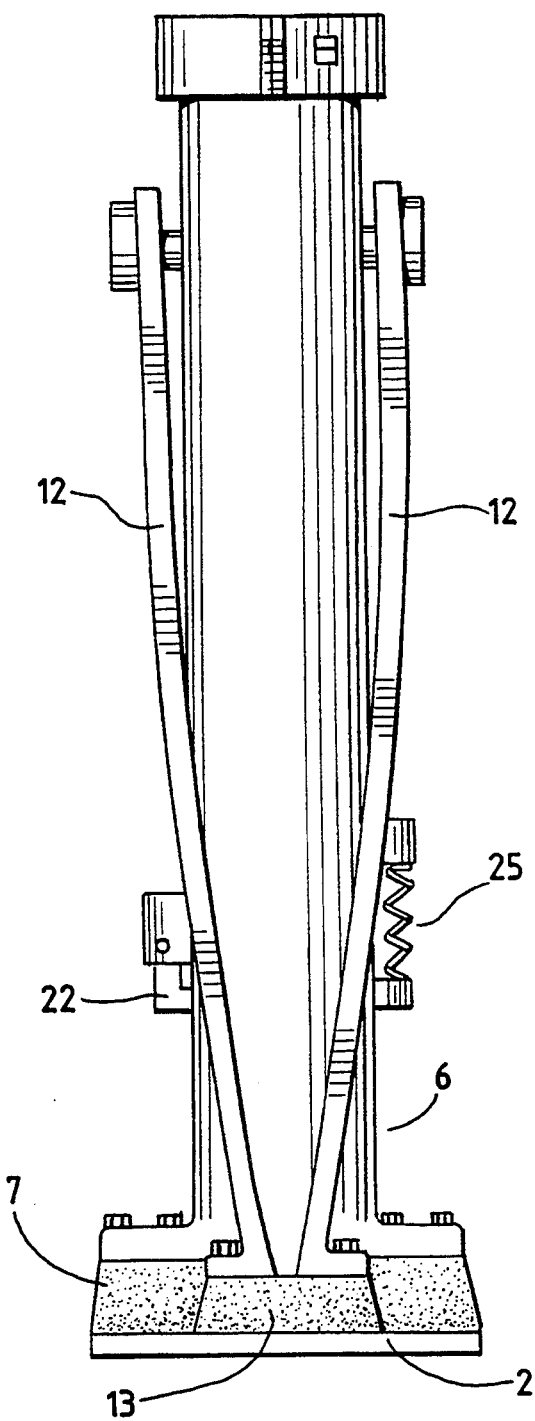

AN ADJUSTABLE RESILIENT FOOT PROSTHESIS

The present invention relates to an orthopedic foot according to the preamble of claim 1.

It is well known that it is troublesome for people wearing a prosthetic foot to walk downhill. In those cases where the person wearing a foot prosthesis is not able to adjust the foot angle, it is only the heel which has contact with the road surface or like surface when walking down a steep slope. Over a given number of degrees of foot angle, it is difficult to hold back, or brace the body, so that the knee will not collapse (due to the absence of important muscle groups). Consequently, the wearer of the prosthesis will often choose to walk sideways down a slope.

Furthermore, the wearer of a prosthetic foot which lacks the possibility of adjustment in the height direction finds it problematic to change to a shoe of different heel height, and of quickly choosing to walk without shoes. Individual adjustment of the foot in a vertical or height direction also alleviates problems associated with back pains and worn hips.

An adjustable prosthetic foot is known, for instance, from the U.S. Pat. No. 2,749,557, although this prosthetic foot can only be adjusted in three different angular positions.

The Swedish Published Specification No. 456 134 teaches a prosthestic foot with which the angular positions thereof can be adjusted by means of a screw provided in the heel of the foot. In order to change the angular position of the foot, it is necessary for the wearer of the prosthesis to turn the screw an appropriate number of turns, which requires a certain amount of effort on the part of the wearer. The angle-changing principle taught by this publication has the serious drawback that the length of the leg remains changed, which means that in some positions, the wearer may limp on the right or the left leg.

One object of the present invention is to solve the aforesaid problems and to provide an adjustable resilient foot prosthesis which can be adjusted to an innumerable number of angular positions quickly and smoothly. Another object of the invention is to provide a foot prosthesis which is light in weight and which will thrust the foot forwards when a walking step is completed and which will also eliminate those drawbacks associated with earlier known techniques. The solution to these problems is set forth in the characterizing clause of claim 1.

FIG. 3 is a rear view of the foot.

Figure 1:
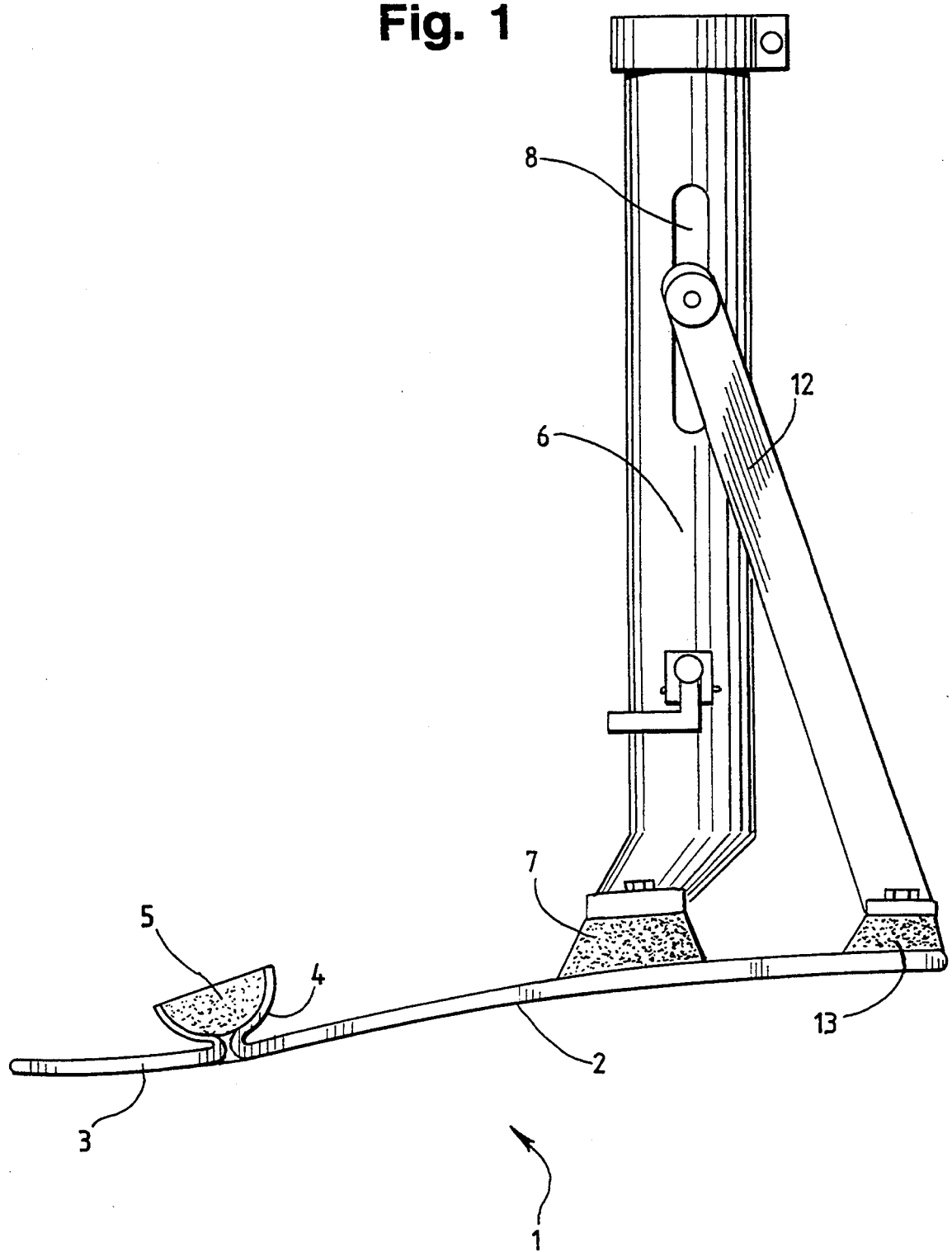
FIG. 1 illustrates a preferred embodiment of the invention.
Figure 2:
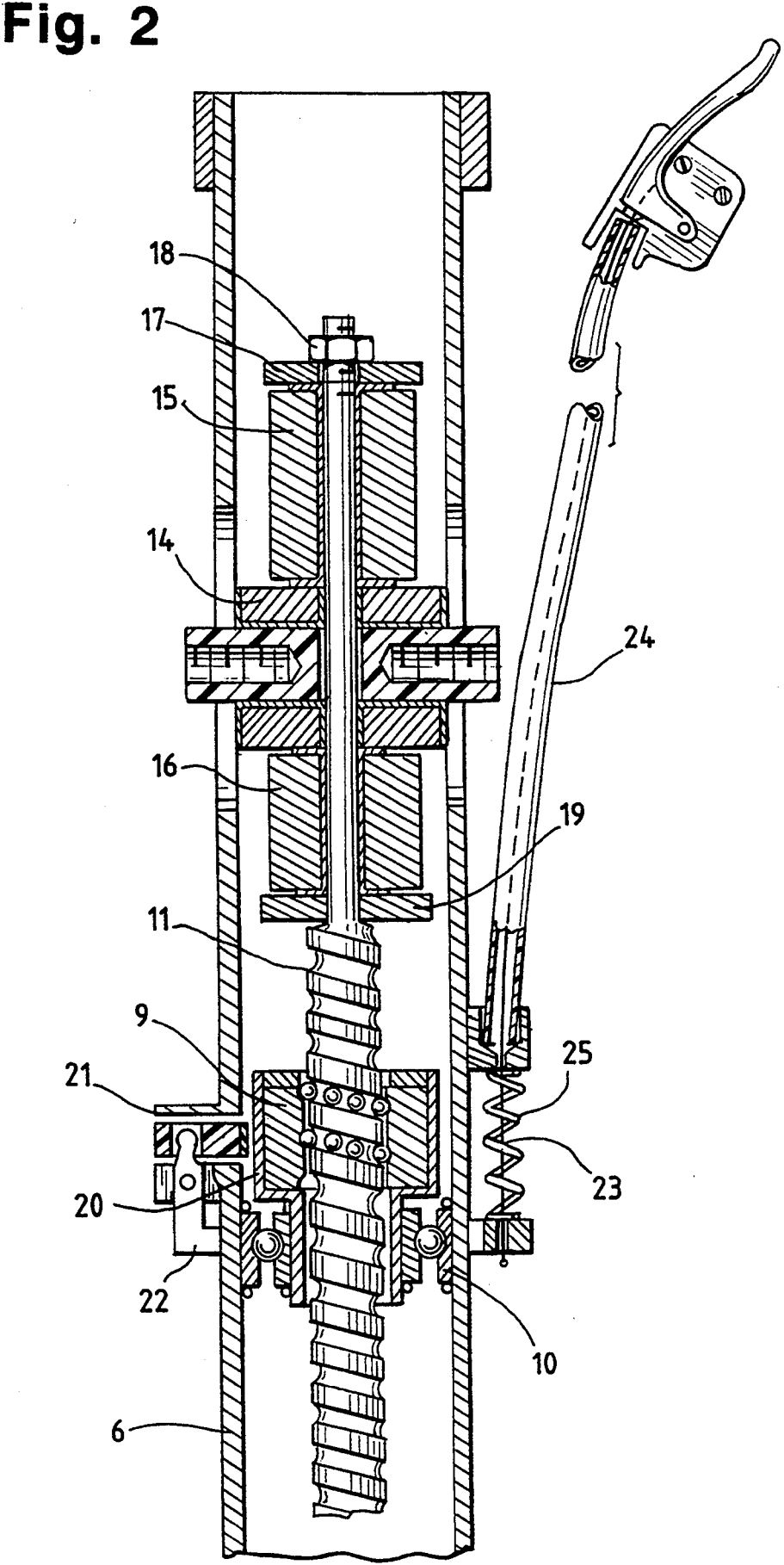
FIG. 2 is a sectional view through a hollow cylindrical body taken through the points at which the brace is attached to the cylindrical body. The threads of the screw and its associated balls are drawn in another section plane, in order to improve illustration.

The orthopedic foot illustrated in FIGS. 1–3 comprises a bar or foot blade 1, preferably made of carbon fibre material and intended to be attached to a bottom part (not shown in the drawings) which functions as a walking sole and which is manufactured from some kind of rubber material, for example. The foot blade preferably comprises two parts, namely a main blade 2 and a toe blade 3. The length of the toe blade is preferably smaller than half the length of the main blade. The forward part of the main blade 2 and the rearward part of the toe blade 3 are curved upwards such as to form therebetween a cup-shaped part 4. A spring device 5, preferably made of an elastic material, such as rubber, is fitted in said cup-shaped part.

Arranged approximately centrally on the main blade 2 in the direction of its longitudinal axis is an upper foot-part which includes a hollow cylindrical body 6 which is attached to the foot-blade through the intermediary of rubber spacing blocks 7, 13 so as to obtain relative movement between the foot-blade and the upper foot-part. The upper foot-part is intended for attachment to a lower leg-part or to some other prosthesis, in accordance with a conventional method. The cylindrical body 6 is provided with two mutually opposed slots which extend in the direction of the longitudinal axis of said body. A ball nut 9 is mounted on journal bearings 10 in the lower part of the tubular body 6 so that said body can be rotated with the rotational axis lying along the cylinder axis of the cylindrical body. Extending in the ball nut 9 is a partially screw-threaded shaft which approximately midway of an upper non-threaded part is connected to a two-part brace 12 which extends from said shaft to the rear end of the foot blade 1, where it is connected to the foot blade through the intermediary of an elastic spacing block 13. This brace is comparable to the heel tendon of the human foot. A moveably mounted nylon piston 14 embraces the shaft in the region of the upper attachment point of said brace to said shaft. One function of the piston is to form a support for an upper spring 15 and a lower spring 16, preferably made of an elastic, rubber material, and also to centre movement in the cylindrical body 6. The upper spring is also supported by a washer 17 which is located on tile upper end of the shaft and which is locked by means of a nut 18. The bottom spring is also supported by a washer 19 which is mounted at the start of the screw-thread on the shaft, which is approximately midway along the shaft. The upper, non-threaded part of the shaft is bevelled in the longitudinal direction, therewith to prevent rotational movement. The threaded part of the shaft may move freely in the ball nut, as previously mentioned. This movement is activated by the prosthesis wearer but can be locked, however, by preventing rotation of the ball nut 9. This is effected by applying a braking force on the outer cylindrical surface 20 of the ball nut with the aid of a brake means. This brake means comprises a brake shoe or brake block 21 which lies against the cylindrical surface 20 when the brake is applied.

The brake means may alternatively have the form of a toothed ring placed around the cylindrical surface 20 and a pawl which engages said toothed ring when the brake is applied. This preferred variant includes a brake shoe 21 which, via an arm 22 which extends around half the circumference of the cylindrical body, is attached to a brake wire 23 which extends to a height along the leg appropriate to the wearer of the prosthesis. The casing 24 of the brake wire is attached to the outer surface of the cylindrical body 6 by means of an attachment device. The actual wire 23 itself is attached to the arm 22 via a spring 25.

The prosthestic foot functions in the following manner: When the foot is attached to the lower leg of the user and the ball nut is in its braking position, such that the brake shoe 21 lies against the outer cylindrical surface 20 of the ball nut, the brace 12, which extends from the cylindrical body 6 to the foot blade 1, will function similar to the heel tendon of a human foot. The nylon piston to which the upper part of the brace 12 is attached moves up and down, in response to movement of the centre of gravity between heel and toe part. The two springs which transmit the force from the brace to the shaft in the ball screw then mutually coact with the rubber springs mounted in the foot blade so that the foot is thrust forwards to some extent upon completion of a walking step.

When the wearer intends to walk down a steep slope or to change the angle of the foot for some other reason, for instance to change shoes, etc., the wearer manoeuvres the brake wire so that the brake shoe will no longer abut the ball nut. The shaft extending through the ball nut can now be moved axially, thereby rotating the ball nut. Adjustment to the desired angular position can be effected by applying a requisite force on the toe part or the heel part of the prosthestic foot.

The use of a ball nut and associated spindle has made it possible within prosthesis technique to convert linear motion to rotational motion with a limited force. The realization of this with this particular application is fundamental to the advent of this prosthesis.

The inventive prosthetic foot has many advantages. It stands flat and stable on the underlying support surface.

It constantly follows the direction in which the user walks, which eliminates wear on hip joints and on the spine.

The angle of the foot can be adjusted so as to enable the wearer to use shoes of differing heel heights and enables the angle of the foot to be readily adjusted to conform to the nature of the underlying support surface.

It will be understood that the present invention is not restricted to the aforedescribed and illustrated embodiment and that modifications and changes can be made within the scope of the invention as defined in the following claims.

I claim:

1. An artificial foot comprised of:
   a foot blade and a hollow housing, wherein said foot blade extends at an angle to and is connected to said housing so as to permit relative movement between said housing and said foot blade,
   an elongated brace for adjusting the angular position of said foot blade with respect to said housing, wherein one end of said brace is displaceably and adjustably attached to said housing by means of attachment to a shaft with a ball screw engaged with a ball nut disposed within said housing, wherein the other end of said brace is connected to said foot blade so as to permit relative movement between said housing and said foot blade, and
   brake means for selectively locking and unlocking said ball nut with respect to said housing in order to adjust the angular position of said foot blade with respect to said housing.

2. An artificial foot according to claim 1, further comprising a nylon piston attached to said brace and engaging said shaft by means of springs when said ball nut is locked or unlocked with respect to said housing.

3. An artificial foot according to claim 2, further comprising a brake shoe to selectively either abut said ball nut to prevent rotational movement of said ball nut, or allow rotational movement of said ball nut.

4. An artificial foot according to claim 3, further comprising an arm mounted to said brake shoe and a brake wire attached to said arm, whereby said brake wire may be manipulated in a region near the thigh of a wearer of said artificial foot in order to selectively lock and unlock said ball nut.

* * * * *